United States Patent [19]
Yoshizawa et al.

[11] 4,371,440
[45] Feb. 1, 1983

[54] METHOD OF TREATING A WASTE WATER RICH IN PROTEIN

[75] Inventors: Kiyoshi Yoshizawa, Tokyo; Kenichi Otsuka, Higashiooizumi; Kikuo Nojiro, Machida; Takeo Koizumi, Yokohama; Katsuyoshi Mitsutomi, Ushiku; Seiji Nakamura, Kashiwa, all of Japan

[73] Assignees: National Tax Administration Agency; Toh Zinc Company Limited, both of Tokyo, Japan

[21] Appl. No.: 304,965

[22] Filed: Sep. 23, 1981

[51] Int. Cl.³ .................................................. C02F 3/34
[52] U.S. Cl. .................................... 210/601; 210/611; 210/905; 435/921; 435/940

[58] Field of Search ............... 210/611, 620, 631, 601, 210/905; 435/921–924, 940–943

[56] References Cited

U.S. PATENT DOCUMENTS 3,751,338  8/1973  Farris .......................... 210/611 X
4,183,807  1/1980  Yoshizawa et al. ............ 210/611

FOREIGN PATENT DOCUMENTS 53-19673  2/1978  Japan .......................... 210/611

Primary Examiner—Thomas G. Wyse
Attorney, Agent, or Firm—Browdy & Neimark

[57] ABSTRACT

Newly isolated yeasts assimilating a high amount of protein are added to a waste water rich in protein thereby making such yeasts assimilate protein, so that the B.O.D. of the waste water is efficiently decreased.

1 Claim, No Drawings

METHOD OF TREATING A WASTE WATER RICH IN PROTEIN

The present invention relates to a method of treating and purifying a waste water rich in protein, for example, the waste water from a fish processing plant, the waste water from a meat processing plant, waste water containing blood from a slaughterhouse, and so forth.

In general, a waste water from a food production plant contains a high amount of carbohydrate and protein, and therefore if it is discharged without any treatment, rivers become rich in nutrients resulting in pollution of the rivers. However, it had hitherto been difficult to remove carbohydrate and protein contained in a waste water.

The inventors of the present invention had researched for seeking microorganisms capable of directly assimilating carbohydrate or protein, and as a result succeeded in isolating yeasts capable of directly assimilating carbohydrate, particularly polysaccharide. The isolated yeasts had respectively belonged to one of the group of genus Saccharomyces, genus Candida and genus Hansenula. The isolated yeasts had been very useful for treating waste water, for example, the waste water from an alcoholic liquor production plant, from a starch production plant and so forth, because of the yeasts' ability to directly assimilate starch, etc. However, the isolated yeasts had been very poor at assimilating protein, and therefore they had not been utilized to treat waste waters rich in protein.

Consequently, the inventors of the present invention had researched under the notion that if microorganisms which can directly assimilate protein are isolated, waste water rich in protein can be treated and purified at one stroke by using only the said microorganisms or by taking the said microorganisms in combination with the microorganisms assimilating carbohydrate. As a result, the inventors of the present invention succeeded in finding microorganisms respectively belonging to one of the group of genus Saccharomyces, genus Candida and genus Trichosporon, which can directly assimilate protein and therefore can treat and purify a waste water at one stroke.

Four strains newly isolated are unknown strains which can assimilate a high amount of protein. These strains were identified as respectively belonging to one of the group of genus Saccharomyces, genus Candida and genus Trichosporon, and they were deposited with the Fermentation Research Institute, Agency of Industrial Science and Technology.

These strains are shown as follows:
1. Saccharomyces sp. KB 14-1, FERM-P No. 4886
2. Candida sp. KB 8, FERM-P No. 4885
3. Candida sp. 3B, FERM-P No. 4884
4. Trichosporon sp. 1B, FERM-P No. 4887

The details of taxonomic studies of these yeasts are shown as follows:
Saccharomyces sp. KB 14-1, FERM-P No. 4886
Growth in malt extract (25° C., cultivation for two days):
   Cell is spherical or short-oval.
   Sediment is produced.
Growth on malt agar (17° C., cultivation for one month):
   Streak culture is cream-colored.
Ascospores formation: Two to four ascospores are formed.
Fermentation: Glucose, sucrose, maltose, galactose and raffinose (⅓) are fermented.
Nitrate assimilation: Negative
Candida sp. KB 8, FERM-P No. 4885
Growth in malt extract (25° C., cultivation for two days):
   Cell is spherical.
Slide culture: Pseudomycelium is formed.
Ascospores formation: Negative
Candida sp. 3B, FERM-P No. 4884
Growth in malt extract (25° C., cultivation for two days):
   Cell is cylindrical or long-oval.
Slide culture: Pseudomycelium is formed.
Ascospores formation: Negative
Trichosporon sp. 1B, FERM-P No. 4887
Growth in malt extract (25° C., cultivation for two days):
   Cell is cylindrical.
   Propagation is done by budding and fission.
Slide culture: Arthrospore is formed.

|  | Sugar Assimilation | | | |
| --- | --- | --- | --- | --- |
|  | S.sp.KB 14-1 | C.sp.KB 8 | C.sp.3B | T.sp.1B |
| Glucose | + | + | + | + |
| Galactose | + | + | + | + |
| Sucrose | + | + | + | ± |
| Maltose | + | + | + | + |
| Lactose | − | − | + | − |
| Arabinose | − | + | − | − |

The newly isolated strains used in the present invention are not particularly different from the known strains of each genus in point of usual observation. However, they possess distinguishing character in remarkably assimilating protein, which character has hitherto been unknown. When known strains are added to a waste water rich in protein, they hardly propagate therein. On the contrary, each strain of the present invention assimilate protein speedily and propagate remarkably, thereby sedimenting themselves. Therefore, when the incubation mixture of each strain of the present invention is added to a waste water rich in protein, 60–90% of the protein is assimilated, thereby resulting in the conspicuous decrease of the B.O.D. of the waste water. Thereafter the separated cells can be utilized as an animal feed.

The method of treating waste water according to the present invention is widely applicable to various waste waters rich in protein. For example, it is applicable to the waste water from fish processing plants, from meat processing plants from tofu (soybean curd) a production plants and from slaughterhouses, and so forth.

The treatment of waste water according to the present invention is carried out by adding the incubation mixture of at least yeast from the group of the yeasts assimilating a high amount of protein, with or without at least one yeast assimilating starch, to the waste water subjected to a pretreatment such as filtration, centrifugal separation, chemical treatment, and so forth. The incubation mixture may be used alone, together with a different incubation mixture, or together with various incubation mixtures, as the case may be.

As an incubation mixture, one that was cultured from a seed culture in large quantities may be used, and also the cells cultured by the treatment of waste water in large quantities may by returned to be used. The inoculum size is preferably about $10^5$-$10^8$ cells/ml, but it may be varied according to the length of the period of cultivation.

The temperature of cultivation is preferably about 20°-40° C., but even if at 20° C., or below, it is possible to perform the waste water treatment in case that the cultivation is carried out for a long time. The cultivation is carried out under an aerobic condition such as stirring, ventilation and so forth.

In the treatment of the present invention, if necessary, as a nutrient, sources of phosphorus or sources of nitrogen, for example ammonium chloride, etc., may be added to a waste water.

In the case when the inoculum size of the cells is low, the growth of yeasts requires about two days if the waste water to be treated has a C.O.D. of several hundreds ppm or below; however, in the case when the inoculum size of the cells is sufficient, the treatment may be complete within one day if a C.O.D. of the waste water is 500 ppm or above.

The removal rate of C.O.D. by the removal of yeasts is generally between 60 and 95%.

The waste water obtained by the treatment of a waste water rich in protein by use of a strain of the present invention is fed to an activated sludge treating tank as it is, or after the cells have been separated therefrom, or after it has appropriately been mixed with a waste water, etc., having a decreased C.O.D., so that it may be more effectively removed of C.O.D. In this case, it is also possible to separate the cells to a certain extent so as to utilize as feed, which cells exist in the waste water in large quantities, but it is also convenient, from the viewpoint of the operation of waste water treatment, that the waste water be directly fed into an activated sludge tank as it is, without specially separating the cells. The yeasts fed into the activated sludge tank become the nutrient of the activated sludge, especially protozoa, thereby resulting in increasing the activity of the sludge. Furthermore, the removal of sludge from the bed does not occur and therefore such waste water is very advantageous for the activated sludge treatment.

As the activated sludge treating tank, it is possible to use any type usually used, such as a lagoon, a trickling filter process and so forth; however, one which is convenient for the use is the activated sludge treating tank in which a bed such as a honeycomb, etc., is applied with the activated sludge.

The activated sludge treatment is carried out in such a way that the waste water is ventilated by means of an air sprayer while the cells being contained therein and circulated through the activated sludge zone are applied to a honeycomb bed. The circulation dwelling time is sufficiently about 10 to 30 hours.

As a result of this treatment, a C.O.D. of 500 ppm (including the yeast cells) of the waste water to be treated is reduced to about 20 to 50 ppm (after the microorganisms have naturally been sedimented). In this case, it is also possible to separate forcibly the microorganisms by coagulation precipitation using a coagulating agent or centrifugal separation by means of a centrifugal separator to thereby force separation without allowing natural sedimentation.

As a treatment of coagulation precipitation by the use of a coagulating agent, a coagulation process is effective in which, for example, ferric chloride, polyaluminum chloride and polyacrylamide are used jointly.

In this coagulation process, the waste water to be treated containing the cells has ferric chloride added thereto while it is stirred. Due to this addition treatment, the pH decreases, and therefore the pH is regulated to a pH of between 6.5 and 7.5, preferably 7.0, by the use of an alkaline solution such as caustic soda solution, etc. Such a pH value is required for the formation of huge floc. With the increase of iron ion, amount of C.O.D. decreases. However, the addition iron remaining in large quantities is not economical and results in the remaining of iron ion in the treated liquid, so that this treatment is not desirable. Accordingly, preferably it is necessary that the addition correspond to a concentration of between 100 and 300 ppm as ferric ion. Under the condition of the pH adjustment as described above, a 10% solution of polyaluminum chloride is added to the waste water in an amount of between about 200 and 300 ml per 1 $m^3$ of waste water, and moreover about 10 ppm of polyacrylamide is added thereto thereby making floc huge. The constant speed sedimentation velocity of the produced floc is as large as 5-6 m/hr. and accordingly the separation and removal of the floc by coagulation precipitation is sufficiently possible. The obtained precipitate can be easily separated off by filtration.

The final C.O.D. of the waste water becomes 5-30 ppm, and such a waste water can be discharged as it is without any treatment.

As described above, the treating method of waste water according to the present invention has succeeded in reducing a C.O.D. of waste water rich in protein to 5-30 ppm by treating the waste water rich in protein with yeasts assimilating a high amount of protein, which yeasts belong to one of the group of genus Saccharomyces, genus Candida and genus Trichosporon, and thereafter by treating with an activated sludge. Therefore, the present invention is very useful for the treatment of waste water rich in protein.

Moreover, the propagated cells of the strain used are very useful, because they can be utilized as an animal feed, etc.

Hereinafter, practical examples will be shown.

PRACTICAL EXAMPLE 1

50 ml of the bovine serum (C.O.D. 25000 ppm, pH=7.0) and 2 μl of a 10% NaClO solution were each put in each of two 500 ml shaker flasks, and one of the two flasks prepared above was inoculated with Candida sp. 3B, FERM-P No. 4884 at an inoculum size of $10^7$/ml, and another flask was inoculated with Trichosporon sp. 1B, FERM-P No. 4887 at an inoculum size of $10^7$/ml. Subsequently, after the incubation with shaking at 30° C. for 96 hours, the yeasts were separated from each incubation mixture by centrifuging and each resultant supernatant liquid was analyzed respectively.

Each C.O.D. removal rate was obtained as follows.

| C.O.D. Removal Rate (%) | |
|---|---|
| Candida sp. 3B, FERM-P No. 4884 | 71.0 |
| Trichosporon sp. 1B, FERM-P No. 4887 | 56.0 |

PRACTICAL EXAMPLE 2

Sample (a): the liquid (C.O.D. 26000 ppm) of blood waste water diluted 10 times and Sample (b): the liquid (C.O.D. 767 ppm) of slaughterhouse waste water diluted 10 times were respectively treated in the same manner as Practical Example 1. Each of the resultant supernatant liquids was analyzed.

Each C.O.D. removal rate was obtained as follows.

| C.O.D. Removal Rate (%) | Sample | |
|---|---|---|
| | (a) | (b) |
| Candida sp. 3B, FERM-P No. 4884 | 82.0 | 71.0 |
| Trichosporon sp. 1B, FERM-P No. 4887 | 79.1 | 64.0 |

PRACTICAL EXAMPLE 3

50 ml of the liquid (C.O.D. 26500 ppm, crude protein 2.1%, total sugars 0.75%) of blood waste water diluted 10 times and 2 μl of a 10% NaClO solution were each put in each of four 500 ml shaker flasks, and then the initial pH of each of the liquids to be treated was respectively adjusted to 5.0, 6.0, 6.5, and 7.0 individually. Subsequently, each resultant liquid was inoculated with Candida sp. 3B, FERM-P No. 4884 at an inoculum size of $4.2 \times 10^6$/ml. After the cultivation with shaking at 30° C. for 96 hours, the number of cells of each cultivated liquid was measured. Moreover, after the separation of yeasts, The C.O.D. removal rate and crude protein removal rate of each resultant supernatant liquid were determined.

| Initial pH | Cell Count ($\times 10^7$/ml) | Removal Rate (%) | |
|---|---|---|---|
| | | C.O.D. | Crude Protein |
| 5.0 | 4.2 | 53 | 76 |
| 6.0 | 9.6 | 86 | 81 |
| 6.5 | 10.8 | 95 | 96 |
| 7.0 | 11.2 | 95 | 87 |

PRACTICAL EXAMPLE 4

50 ml of the waste water (C.O.D. 18690 ppm, crude protein 1.75%, phosphorus 424 ppm) of boiled mackerel and 2 μl of a 10% NaClO solution were each put in each of two 500 ml shaker flasks, and then the initial pH of each waste water to be treated was respectively adjusted to 4.5. One of the two flasks prepared above was inoculated with Saccharomyces sp. KB 14-1, FERM-P No. 4886 at an inoculum size of $10^8$/ml, and another flask was inoculated with Candida sp. KB-8, FERM-P No. 4885 at an inoculum size of $10^8$/ml. Each flask was incubated with shaking at 30° C. for 96 hours, and after the separation of yeasts each of the resultant supernatant liquids was respectively analyzed.

The results thereof are shown in the following table.

| | Removal Rate (%) | | |
|---|---|---|---|
| | C.O.D. | Crude Protein | Phosphorus |
| Saccharomyces sp. KB 14-1, FERM-P No. 4886 | 70 | 50 | 46 |
| Candida sp. KB-8, FERM-P No. 4885 | 53 | 40 | 61 |

PRACTICAL EXAMPLE 5

100 ml of diluted waste water (pH=4.5, C.O.D. 7943 ppm) containing blood was put in a 500 ml shaker flask, and then the flask prepared above was inoculated with Saccharomyces sp. KB 14-1, FERM-P No. 4886 at an inoculum size of $10^7$/ml. Subsequently, in the course of the incubation with shaking at 30° C., every 24 hours 75 ml of the incubation mixture was removed from the flask and in exchange for the removed incubation mixture 75 ml of the diluted waste water (pH=4.5, C.O.D. 7943 ppm) containing blood was added into the flask.

The C.O.D. and the number of cells of each incubation mixture removed every 24 hours were measured.

The results are shown in the following table.

| | 1 Day | 2 Days | 3 Days | 4 Days |
|---|---|---|---|---|
| C.O.D. ppm | 3238 | 3619 | 3330 | 3619 |
| Cell Count ($\times 10^8$/ml) | 8.0 | 5.8 | 5.5 | 6.5 |

What is claimed is:

1. A method of treating a waste water rich in protein, comprising:
   adding to a waste water rich in protein at least one yeast capable of assimilating a high amount of protein, said at least one yeast being selected from the group consisting of
   Saccharomyces sp. KB 14-1, FERM-P No. 4886,
   Candida sp. KB 8, FERM-P No. 4885,
   Candida sp. 3B, FERM-P No. 4884, and
   Trichosporon sp. 1B, FERM-P No. 4887, thereby causing said yeast to assimilate protein; and
   flowing the obtained waste water into an activated sludge tank in which the obtained waste water is treated with an activated sludge.

* * * * *